United States Patent [19]
Persson

[11] 3,937,564
[45] Feb. 10, 1976

[54] METHOD FOR TRIMMING OF A SPECIMEN FOR A MICROTOME

[75] Inventor: Karl Göran Algy Persson, Stockholm, Sweden

[73] Assignee: LKB-Produkter AB, Bromma, Sweden

[22] Filed: June 4, 1973

[21] Appl. No.: 366,663

Related U.S. Application Data

[63] Continuation of Ser. No. 170,943, Aug. 11, 1971, abandoned.

[30] Foreign Application Priority Data

Aug. 28, 1970 Sweden............................. 11784/70

[52] U.S. Cl. .................. 350/320; 350/30; 356/168; 83/915.5
[51] Int. Cl.² ........................................ G02B 21/18
[58] Field of Search ........... 350/30, 33, 34, 81, 320; 356/168, 171, 172; 83/915.5

[56] References Cited
UNITED STATES PATENTS

| | | | |
|---|---|---|---|
| 2,614,454 | 10/1952 | Steffen | 350/30 X |
| 3,103,844 | 9/1963 | Persson | 350/81 X |
| 3,324,759 | 6/1967 | Fielding | 83/915.5 X |
| 3,377,898 | 4/1968 | Persson | 350/81 X |
| 3,388,848 | 6/1968 | Youmans et al. | 350/81 X |
| 3,398,633 | 8/1968 | Raivio | 350/30 X |

*Primary Examiner*—David H. Rubin

[57] ABSTRACT

A method for trimming of a specimen which is to be sectioned in a microtome to locate that part of the specimen which is of interest, comprising the superimposing in a microscope of the image of a cut section on the image of the specimen surface.

1 Claim, 1 Drawing Figure

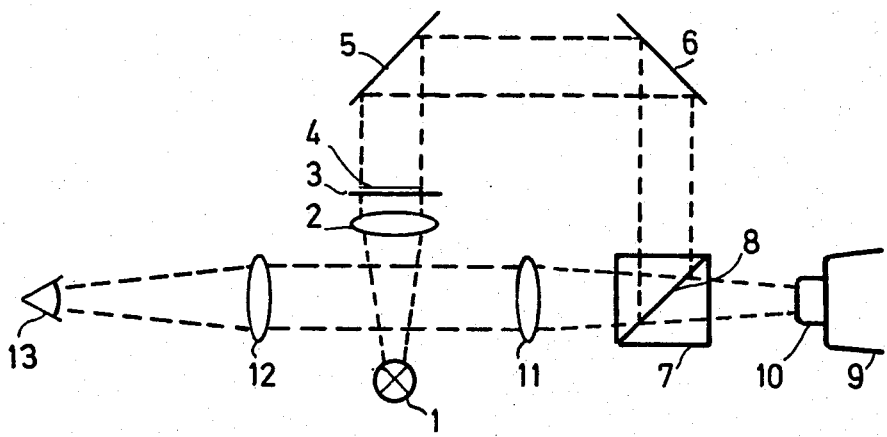

METHOD FOR TRIMMING OF A SPECIMEN FOR A MICROTOME

This is a continuation of application Ser. No. 170,943, filed Aug. 11, 1971 now abandoned.

The present invention relates to a method for trimming of the specimen which is to be sectioned in a microtome to locate that part of the specimen which is to be sectioned.

When a specimen is being sectioned in a microtome the specimen is usually first embedded in a suitable medium whereupon it is cut in a way that e.g. a truncated pyramid is obtained, at the upper surface of which the specimen itself is situated. Generally, however, it is of interest just to section in the microtome some certain part of the specimen, and it is thus desirable that the pyramid is being further cut in such a way that only this part of interest remains. In order to determine the position of this part it is hitherto proceeded in that way that a fairly thick section is cut from the top of the pyramid which section is then suitably stained by a contrast agent. The section is then studied in a microscope whereby the most interesting part of the pyramid surface can be located. The position thereof is then registered either by memory or by means of a scale in the ocular of the microscope. Then the section is removed from the microscope and replaced by the specimen which is introduced in the microscope together with a device, suitable for trimming of the specimen. The specimen is then being trimmed in a way that the previously registered interesting part of the top of the pyramid remains. However, it has been found that it is practically very difficult then to get a complete agreement between the interesting part, determined by sectioning, and that part of the top of the pyramid which later on is sectioned.

It is the purpose of the present invention to provide a method by means of which an exact agreement is obtained between the interesting part determined from the section, and the sectioned part of the pyramid top. The characteristics of the method are obvious from the claims following the specification.

The invention will now be more closely explained with reference to an accompanying drawing schematically showing a device for performing of the method according to the invention.

In the drawing the reference 1 denotes a lamp which via a condensor 2 transilluminates a plate 3 on which a stained specimen section 4 is arranged. Those light beams which are passing through the specimen 4 are via two mirrors 5 and 6 transmitted onto a half-transparent surface 8 in a prism 7. The prism 7 is arranged ahead of a lens 11 which constitutes the objective of a microscope. The microscope further comprises an ocular 12 and in addition an observer 13 is hinted. The device is then designed in a way that a picture of the section 4 is obtainable in the ocular of the microscope. Further a specimen 10, arranged in a specimen holder 9, is shown, the section 4 assumed to be taken from that specimen. As the mirror 8 is partly transparent, a picture of the surface of the specimen 10 will as well be obtained in the ocular of the microscope. The device is then arranged in such a way that the images of the section 4 and of the surface of the specimen 10 are in the same image plane of the objective. The observer 13 thus observes two superimposed images, the image of the stained section 4 as well as the image of the surface of the specimen 10. By means of the image of the specimen 4 it is thus possible to determine exactly which part of the surface of the specimen 10 that is to be cut out for subsequent sectioning. The trimming of the specimen might then either be carried out directly guided by the superimposed image, or might be carried out later according to indications made with the aid of the superimposed image.

The drawing explains the principle of the invention which thus comprises that interesting parts of a specimen surface are chosen by simultaneously observing the specimen surface and the image of a suitably prepared section, cut from the surface, the image of the section being superimposed onto the specimen surface. The condition for this is that an at least partly transparent image of the cut section is obtained in the ocular plane of the microscope. This can of course be achieved in several ways besides that one shown above. The semi-transparent surface 8 could thus be achieved by changing from a totally reflecting surface and a totally transparent surface at a sufficiently high rate and further it is of course possible to obtain the image of the section 4 via a separate objective. It is further possible to achieve the image of the section 4 by illuminating it from above and transferring the reflected light to the surface 8. By varying the intensity of the lamp 1 it is also possible to vary the intensity of the image of the section 4, i.e. to allow the image of the surface of the specimen 10 more or less to appear in desired contrast in relation to the image of the section. On the plate 3 of course a number of different sections could be subsequently placed so that a comparison between those sections and the pyramid surface of the specimen 10 could be quickly made. The plate 3 may also be employed in that way that e.g. an arrow is placed on it which easily could be moved across the plate whereby structural details of the specimen 10 might in a simple way be shown. In addition to the arrow of course suitable scales and grids could be introduced to the plate 3.

We claim:

1. Method of trimming a specimen for sectioning by a microtome comprising the steps of cutting a thin, partly transparent section from said specimen, removing said partly transparent section from said specimen, treating said partly transparent section to provide a contrasting image of a small specimen area of interest, illuminating said partly transparent section and the surface of the specimen from which said section has been cut, providing an optical path, one portion of which extends through said partly transparent section, for simultaneously viewing optically superimposed images of said illuminated partly transparent section and the surface of the specimen from which said section has been cut in a beam combining microscope to identify the location of the small specimen area of interest on the surface of said specimen by reference to the corresponding visible location on said partly transparent section, and further trimming said specimen by reference to said superimposed images.

* * * * *